US012678459B2

(12) United States Patent
Kang et al.

(10) Patent No.: US 12,678,459 B2
(45) Date of Patent: Jul. 14, 2026

(54) PHARMACEUTICAL COMPOSITION FOR PREVENTING OR TREATING COVID-19 COMPRISING NANO-SIZED GRAPHENE OXIDE COMPOSITE AND METHOD USING SAME

(71) Applicants: INBCT Co., LTD., Hwaseong-si (KR); SEOUL NATIONAL UNIVERSITY R&DB FOUNDATION, Seoul (KR)

(72) Inventors: Kyung Sun Kang, Seoul (KR); Jaechul Ryu, Seoul (KR)

(73) Assignees: INBCT Co., Ltd., Hwaseong-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 499 days.

(21) Appl. No.: 18/013,858

(22) PCT Filed: Jun. 30, 2021

(86) PCT No.: PCT/KR2021/008249
§ 371 (c)(1),
(2) Date: Dec. 29, 2022

(87) PCT Pub. No.: WO2022/005195
PCT Pub. Date: Jan. 6, 2022

(65) Prior Publication Data
US 2023/0285454 A1      Sep. 14, 2023

(30) Foreign Application Priority Data

Jun. 30, 2020    (KR) ........................ 10-2020-0080491
Jun. 29, 2021    (KR) ........................ 10-2021-0084753

(51) Int. Cl.
| | |
|---|---|
| A61K 33/44 | (2006.01) |
| A01N 59/00 | (2006.01) |
| A23K 20/20 | (2016.01) |
| A23L 29/00 | (2016.01) |
| A23L 33/16 | (2016.01) |
| A61K 9/14 | (2006.01) |
| A61P 31/14 | (2006.01) |

(52) U.S. Cl.
CPC .............. A61K 33/44 (2013.01); A01N 59/00 (2013.01); A23K 20/20 (2016.05); A23L 29/015 (2016.08); A23L 33/16 (2016.08); A61K 9/14 (2013.01); A61P 31/14 (2018.01)

(58) Field of Classification Search
CPC ........... A61K 33/44; A61K 9/14; A61P 31/14
See application file for complete search history.

(56) References Cited

FOREIGN PATENT DOCUMENTS

| | | |
|---|---|---|
| CN | 105832767 A | 8/2016 |
| KR | 10-2014-0100235 A | 8/2014 |

OTHER PUBLICATIONS

Ye et al (ACS Applied Materials and Interfaces, 2015, vol. 7, pp. 21571-21579) (Year: 2015).*
Raghav et al (Medical Hypotheses, Jun. 24, 2020, vol. 144, pp. 1-3) (Year: 2020).*
Park et al (Nano Letters, 2009, vol. 9, pp. 1593-1597) (Year: 2009).*
Office Action of the Korean Intellectual Property Office in related Korean Patent Appl. 10-2021-0084753, dated Apr. 21, 2023, 10 pages.
Raghav, P.K. et al., "Are graphene and graphene-derived products capable of preventing COVID-19 infection?" Medical Hypotheses, vol. 144, Issue 110031, pp. 1-3, Jun. 24, 2020.
Ye, S. et al., "Antiviral Activity of Graphene Oxide: How Sharp Edged Structure and Charge Matter," ACS Appl. Mater. Interfaces, vol. 7, p. 21571-21579, Sep. 15, 2015.
Uskokovic, V., "Why have nanotechnologies been underutilized in the global uprising against the coronavirus pandemic?" Nanomedicine (Lond.), vol. 15, Issue 17, pp. 1719-1734, May 28, 2020.
Palmieri, V. et al., "Can graphene take part in the fight against COVID-19?" Nano Today, vol. 33, Issue 100883, pp. 1-4, May 7, 2020.
English Translation of International Search Report and Written Opinion dates Oct. 8, 2021 in counterpart International Patent Application No. PCT/KR2021/008249, 12 pages.

* cited by examiner

*Primary Examiner* — Mark V Stevens
(74) *Attorney, Agent, or Firm* — Bochner PLLC; Andrew D. Bochner

(57) ABSTRACT

Provided are a pharmaceutical composition for preventing or treating a coronavirus infection or infectious disease, a composition for disinfection, and a health functional food or feed composition, all including nano-sized graphene oxide, and a method of using the same. Since the nano-sized graphene oxide or a complex thereof has anti-coronavirus activity, the graphene oxide may be used for prevention or treatment of a coronavirus infection, or disinfection of coronaviruses.

11 Claims, 7 Drawing Sheets

Antiviral activity of nanoGo against PEDV and BCoV

1

PHARMACEUTICAL COMPOSITION FOR PREVENTING OR TREATING COVID-19 COMPRISING NANO-SIZED GRAPHENE OXIDE COMPOSITE AND METHOD USING SAME

TECHNICAL FIELD

The present disclosure relates to a pharmaceutical composition for preventing or treating coronavirus infections, such as COVID-19, including a nano-sized graphene oxide or a composite thereof, and a method of preventing or treating coronavirus infections by using the same.

BACKGROUND ART

Coronavirus is an RNA virus that refers to viruses belonging to the family Coronaviridae. Coronaviruses are found in a variety of mammals, including humans, as well as birds. Coronaviruses are known to cause respiratory and digestive infectious diseases. Avian infectious bronchitis virus (IBV), porcine epidemic diarrhea virus (PEDV), feline infectious peritonitis virus (FIPV), bovine coronavirus: BCV) and the like are known to cause coronavirus infectious diseases. Recently, coronaviruses have received attention as a causative agent of severe respiratory symptoms such as severe acute respiratory syndrome (SARS), middle east respiratory syndrome (MERS), and coronavirus disease 2019 (COVID-19).

On the other hand, when graphene oxide is prepared by chemical exfoliation, —OH, —COOH, —C=O, —CHO, etc. with oxygen are attached to an edge of graphene to form the graphene oxide. That is, graphene oxide is made by the addition of oxygen, carbon, and hydrogen elements. Graphene oxides are used in various fields such as biochemical sensors, nanocomposites, and photocatalysts, and recently, research on pharmaceutical uses of graphene oxides is being conducted.

Therefore, it is necessary to confirm antiviral effects of graphene oxide, and to develop graphene oxide for various uses such as medicines and disinfectants.

DESCRIPTION OF EMBODIMENTS

Technical Problem

An aspect provides a pharmaceutical composition for preventing or treating a coronavirus infection or infectious disease including a nano-sized graphene oxide or a complex thereof.

Another aspect provides a composition for anti-coronavirus disinfection including a nano-sized graphene oxide or a complex thereof.

Another aspect provides a food composition for preventing or improving a coronavirus infection or infectious disease including a nano-sized graphene oxide or a complex thereof.

Another aspect provides a feed composition for preventing or improving a coronavirus infection or infectious disease including a nano-sized graphene oxide or a complex thereof.

Another aspect provides a method for preventing or treating a coronavirus infection or infectious disease, including administering the pharmaceutical composition including a nano-sized graphene oxide or a complex thereof to a subject.

Another aspect provides a method for disinfecting coronavirus including spraying, applying, scattering, sprinkling, washing, or a combination thereof with a composition for anti-coronavirus disinfection including nano-sized graphene oxide or a complex thereof in the air, on a surface of an object, or on a mammal other than a human.

Solution to Problem

An aspect is to provide a pharmaceutical composition for preventing or treating a coronavirus infection or infectious disease including a nano-sized graphene oxide or a complex thereof.

The term "graphene", used herein, refers to one of allotropes of carbon, and a material forming a two-dimensional planar crystal structure of a widely spread hexagonal honeycomb shape, where carbon atoms are present at vertices of a hexagon (sp2 bond). Graphene may exist in a stable structure of a film one atom thick.

The term "graphene oxide (GO)", used herein, refers to a material in which various oxidized functional groups (—OH, —COOH, —C=O, —CHO, etc.) are attached to an edge of graphene, and which forms several to dozens of layers.

The graphene oxide may be obtained by a method known to those skilled in the art. The graphene oxide is obtained by primarily cutting a lump of graphite by applying mechanical/thermal energy, and exfoliating by a mechanical or chemical method to obtain a granulated graphene oxide.

The term "nano-sized graphene oxide (nanoGO)", used herein, refers to a material prepared in a form of particles having a size of a nanometer level by applying a predetermined stimulus to a graphene oxide, and the size in a nanometer-level may be about 500 nm or less, about 400 nm or less, about 300 nm or less, about 200 nm or less, about 100 nm or less, about 90 nm or less, about 80 nm or less, about 70 nm or less, about 60 nm, or about 50 nm or less in diameter. For example, the nano-sized graphene oxide may be prepared by applying ultrasonic waves to a graphene oxide (for example, by tip-sonification).

An average size of the graphene oxide may be about 1 nm to about 50 nm, about 1 nm to about 45 nm, about 1 nm to about 40 nm, about 1 nm to about 35 nm, about 1 nm to about 30 nm, about 1 nm to about 25 nm, about 1 nm to about 20 nm, about 1 nm to about 15 nm, about 1 nm to about 10 nm, about 5 nm to about 50 nm, about 5 nm to about 45 nm, about 5 nm to about 40 nm, about 5 nm to about 35 nm, about 5 nm to about 30 nm, about 5 nm to about 25 nm, about 5 nm to about 20 nm, about 5 nm to about 15 nm, about 5 nm to about 10 nm, about 10 nm to about 50 nm, about 10 nm to about 45 nm, about 10 nm to about 40 nm, about 10 nm to about 35 nm, about 10 nm to about 30 nm, about 10 nm to about 25 nm, about 10 nm to about 20 nm, about 10 nm to about 15 nm, about 15 nm to about 50 nm, about 15 nm to about 45 nm, about 15 nm to about 40 nm, about 15 nm to about 35 nm, about 15 nm to about 30 nm, about 15 nm to about 25 nm, about 15 nm to about 20 nm, about 20 nm to about 50 nm, about 20 nm to about 45 nm, about 20 nm to about 40 nm, about 20 nm to about 35 nm, about 20 nm to about 30 nm, about 20 nm to about 25 nm, about 25 nm to about 50 nm, about 25 nm to about 45 nm, about 25 nm to about 40 nm, about 25 nm to about 35 nm, or about 25 nm to about 30 nm.

A thickness of the graphene oxide may be about 0.3 nm to about 10 nm, about 0.3 nm to about 9.5 nm, about 0.3 nm to about 9 nm, about 0.3 nm to about 8.5 nm, about 0.3 nm to about 8 nm, about 0.3 nm to about 7.5 nm, about 0.3 nm to about 7 nm, about 0.3 nm to about 6.5 nm, about 0.3 nm to about 6 nm, about 0.3 nm to about 5.5 nm, about 0.3 nm to about 5 nm, about 0.5 nm to about 10 nm, about 0.5 nm to about 9.5 nm, about 0.5 nm to about 9 nm, about 0.5 nm to about 8.5 nm, about 0.5 nm to about 8 nm, about 0.5 nm to about 7.5 nm, about 0.5 nm to about 7 nm, about 0.5 nm to about 6.5 nm, about 0.5 nm to about 6 nm, about 0.5 nm to about 5.5 nm, about 0.5 nm to about 5 nm, about 1 nm to about 10 nm, about 1 nm to about 9.5 nm, about 1 nm to about 9 nm, about 1 nm to about 8.5 nm, about 1 nm to about 8 nm, about 1 nm to about 7.5 nm, about 1 nm to about 7 nm, about 1 nm to about 6.5 nm, about 1 nm to about 6 nm, about 1 nm to about 5.5 nm, about 1 nm to about 5 nm, about 1.5 nm to about 10 nm, about 1.5 nm to about 9.5 nm, about 1.5 nm to about 9 nm, about 1.5 nm to about 8.5 nm, about 1.5 nm to about 8 nm, about 1.5 nm to about 7.5 nm, about 1.5 nm to about 7 nm, about 1.5 nm to about 6.5 nm, about 1.5 nm to about 6 nm, about 1.5 nm to about 5.5 nm, about 1.5 nm to about 5 nm, about 2 nm to about 10 nm, about 2 nm to about 9.5 nm, about 2 nm to about 9 nm, about 2 nm to about 8.5 nm, about 2 nm to about 8 nm, about 2 nm to about 7.5 nm, about 2 nm to about 7 nm, about 2 nm to about 6.5 nm, about 2 nm to about 6 nm, about 2 nm to about 5.5 nm, or about 2 nm to about 5 nm.

The nano-sized graphene oxide complex may refer to a complex capable of improving antiviral activity of the graphene oxide which is formed by binding an additional substance/material to the nano-sized graphene oxide, and specifically, the complex may be formed by binding/attaching an additional substance/material such as functional groups, metal particles, magnetic particles, nanoparticles, polymers, peptides, and/or nucleic acids to the nano-sized graphene oxide by physical Vanderwaals force bonding, ionic bonding, hydrogen bonding, covalent and/or non-covalent.

The graphene oxide may have a form of a nanofilm, a nanosheet, a nanowire, a nanorod, a nanotube, a branched nanowire, a nanotetrapod, a tripod, a bipod, a nanocrystal, a nanodot, a quantum wire, or a nanoparticle.

The graphene oxide may be a reduced graphene oxide. The reduced graphene oxide may be prepared by light irradiation, photoreaction, or treating chemicals such as hydrazine.

The nano-sized graphene oxide may exist as a homogenized dispersion. The graphene oxide may maintain a homogenized state without being precipitated in a liquid.

The nano-sized graphene oxide may induce deaths of coronavirus or inhibit entry of coronavirus into cells.

The coronavirus may be selected from the group consisting of alphacoronaviruses, betacoronaviruses, gammacoronaviruses, and deltacoronaviruses.

The term "coronavirus", used herein, refers to a virus belonging to the family Coronaviridae, and having an RNA genome surrounded by an outer membrane. The coronavirus is named after the crown-like shape of the surface spike protein, and has a positive-strand RNA as its genome. This RNA contains information encoding structures of the virus such as nucleocapsid (N), envelope (E), membrane (M), and spike (S) proteins. Coronaviruses self-replicate by penetrating into a host when a receptor binding domain (RBD) of the surface spike (S) protein binds and fuses with a receptor of the host cell.

The coronavirus may be porcine epidemic diarrhea virus (PEDV), canine coronavirus (CCV), feline infectious peritonitis virus (FIPV), bovine coronavirus (BCoV or BCV), avian infectious bronchitis virus (IBV), transmissible gastroenteritis coronavirus (TGEV), severe acute respiratory syndrome coronavirus (SARS-CoV), severe acute respiratory syndrome coronavirus 2 (SARS-CoV-2), middle east respiratory syndrome coronavirus (MERS-CoV), or a combination thereof. SARS-CoV-2 may be a main causative agent of coronavirus infection-2019 (COVID-19).

Viruses are infectious agents that are smaller than bacteria. Viruses are composed of RNA or DNA, which is a genetic material, and proteins surrounding the genetic material. Since a virus cannot metabolize itself, it infiltrates its own DNA or RNA into a host cell and uses the organelles of the infiltrated cell to replicate its genetic material and produce viruses like itself. In this process, the host cell is damaged or destroyed, which may cause a disease in the host.

The coronavirus infectious disease includes not only coronavirus infection, but also any symptoms resulting from it, including fever, cough, dyspnea, sore throat, headache, myalgia, and pneumonia, and complications resulting therefrom. Specifically, the coronavirus infectious disease may be coronavirus cold, coronavirus enteritis, coronavirus diarrhea, coronavirus pneumonia, severe acute respiratory syndrome (SARS), middle east respiratory syndrome (MERS), coronavirus disease 2019 (COVID-19), acute respiratory distress syndrome (ARDS), avian infectious bronchitis, or a combination thereof.

The term "prevention", used herein, refers to any action that suppresses a coronavirus infectious disease or delays an onset thereof by administering a composition, and the term "treatment" refers to any act of improving or beneficially changing symptoms of a coronavirus infectious disease by administering a composition.

The pharmaceutical composition may further include a known active ingredient having antibacterial or antiviral activity. The active ingredient may be oseltamivir, zanamivir, peramivir, ribavirin, azauridin, amantadine, rimantadine, valaciclovir, interferon, immunoglobulin preparation, or a combination thereof.

The pharmaceutical composition may include a pharmaceutically acceptable carrier. The "pharmaceutically acceptable carrier" may refer to a carrier or diluent that does not inhibit biological activity and properties of the injected compound without irritating the organism. Here, "pharmaceutically acceptable" means not inhibiting an activity of an active ingredient and not having more toxicity than a target of the application (prescription) is capable of adapting to. Any kind of a carrier that may be commonly used in the art and is pharmaceutically acceptable may be used as a carrier that may be used in the pharmaceutical composition. Non-limiting examples of the carrier may include lactose, dextrose, maltodextrin, sucrose, sorbitol, mannitol, xylitol, erythritol, maltitol, glycerol, ethanol, starch, acacia rubber, alginate, gelatin, calcium phosphate, calcium silicate, cellulose, methyl cellulose, microcrystalline cellulose, polyvinyl pyrrolidone, water, saline, sterile water, Ringer's solution, buffered saline, albumin injection solution, methylhydroxybenzoate, propylhydroxybenzoate, talc, magnesium stearate, mineral oil, etc. These may be used alone or in combination of two or more. The pharmaceutical composition may be prepared as an oral dosage form or a parenteral dosage form according to a route of administration by a method known in the art, including a pharmaceutically acceptable carrier in addition to the active ingredient. The pharmaceutical composition may be formulated as an oral dosage form such as powders, granules, tablets, capsules, suspensions, emulsions, syrups, aerosols, etc., or as external preparations, suppositories, or sterile injection solutions, each according to a method in the art.

When formulating the pharmaceutical composition, the pharmaceutical composition may be prepared by using a diluent or excipient such as a generally used filler, extender, binder, wetting agent, disintegrant, or surfactant.

When the pharmaceutical composition is prepared as an oral dosage form, the pharmaceutical composition may be prepared in a dosage form of powders, granules, tablets, pills, dragees, capsules, liquids, gels, syrups, suspensions, wafers, etc., according to a known method in the art with a suitable carrier. Examples of suitable pharmaceutically acceptable carriers include sugars such as lactose, glucose, sucrose, dextrose, sorbitol, mannitol, and xylitol, starches such as corn starch, potato starch, wheat starch, celluloses such as cellulose, methylcellulose, ethylcellulose, sodium carboxymethylcellulose, and hydroxypropylmethylcellu-lose, polyvinylpyrrolidone, water, methylhydroxybenzoate, propylhydroxybenzoate, magnesium stearate, mineral oil, malt, gelatin, talc, polyol, vegetable oil, etc. The formulation may be prepared by using a diluent and/or an excipient such as a filler, an extender, a binder, a humectant, a disintegrant, or a surfactant.

When the pharmaceutical composition is prepared as a parenteral dosage form, the pharmaceutical composition may be formulated as injections, transdermal dosage forms, nasal inhalants, and suppositories together with a suitable carrier according to a method known in the art. When the pharmaceutical composition is formulated as an injection, suitable carriers such as sterile water, ethanol, polyols such as glycerol or propylene glycol, or mixtures thereof, and preferably, Ringer's solution, phosphate buffered saline (PBS) containing triethanolamine, or sterile water for injection, an isotonic solution such as 5% dextrose, etc. may be used. When formulated as a transdermal dosage form, the pharmaceutical composition may be formulated as oint-ments, creams, lotions, gels, solutions for external use, pastes, liniments, and air lozenges. When the pharmaceuti-cal composition is formulated as nasal inhalants, the phar-maceutical composition may be formulated in a form of an aerosol spray by using a suitable propellant such as dichlo-rofluoromethane, trichlorofluoromethane, dichlorotetrafluo-roethane, carbon dioxide, etc., and when formulated as suppositories, substrates used therefor include witepsol, tween 61, polyethylene glycols, cacao fat, laurin oil, poly-oxyethylene sorbitan fatty acid esters, polyoxyethylene stearate, sorbitan fatty acid esters, and the like.

The pharmaceutical composition may be administered in a pharmaceutically effective amount, and the term "phar-maceutically effective amount" as used herein means a sufficient amount to treat or prevent a disease at a reasonable benefit/risk ratio applicable to medical treatment or preven-tion. An effective dose level may be determined based on well-known factors in the medical field such as severity of the disease, drug activity, the patient's age, weight, health, sex, and sensitivity to the drug, administration time of the used composition of the present disclosure, an administra-tion route, rate of excretion, treatment period, drugs used in combination with or concurrently with the composition of the present disclosure, etc. For example, the effective amount of the pharmaceutical composition may be about 10 mg to about 10 g, about 100 mg to about 8 g, about 250 mg to about 6 g, about 500 mg to about 4 g, about 500 mg to about 2 g, or about 500 mg to about 1 g. The pharmaceutical composition may be administered by a method in the art via oral, rectal, intravenous, intraarterial, intraperitoneal, intra-muscular, intrasternal, transdermal, topical, intraocular, or intradermal routes. The dosage of the pharmaceutical com-position is within a range of about 0.001 mg/kg to about 100 mg/kg, about 0.01 mg/kg to about 10 mg/kg, or about 0.1 mg/kg to about 1 mg/kg, for an adult, and may be admin-istered once a day, multiple times a day, or once a several days.

The pharmaceutical composition may be administered alone or in combination with a component known to exhibit a therapeutic effect on a known coronavirus infection or infectious disease. Taking all of the above factors into consideration, it is important to administer an amount capable of obtaining the maximum effect with a minimum amount without side effects.

Another aspect provides a composition for anti-corona-virus disinfection including the nano-sized graphene oxide or a complex thereof. The same parts as described above also apply to the composition.

The term "disinfection", used herein, means depriving activity of or killing a pathogenic microorganism or a pathogenic virus. Depriving activity includes inhibiting infection, survival, proliferation, transmission, or a combi-nation thereof of a pathogenic microorganism or pathogenic virus. The composition for disinfection may be formulated as a disinfectant or a cleaning agent. The composition for disinfection may be commercialized as an anti-coronavirus disinfectant for spraying directly on animal-related facilities and animals, and an anti-coronavirus disinfectant and a cleaning agent for washing hands and instruments in animal-related facilities or hospitality establishments requiring hygiene. The graphene oxide may be included in the com-position in an amount of about 1.0 wt % to about 90.0 wt %, about 1.0 wt % to about 80.0 wt %, about 1.0 wt % to about 70.0 wt %, about 1.0 wt % to about 60.0 wt %, about 1.0 wt % to about 50.0 wt %, about 5.0 wt % to about 50.0 wt %, about 10.0 wt % to about 50.0 wt %, about 10.0 wt % to about 40.0 wt %, about 10.0 wt % to about 30.0 wt %, or about 10.0 wt % to about 20.0 wt %.

The composition for disinfection may include a surfac-tant, a chelating agent, a pH adjusting agent, an enzyme, a bleach, a builder, or a mixture thereof as an additive to further enhance the sterilization and disinfection effect by adjusting pH of the composition.

The pH adjusting agent may include an organic acid such as formic acid, acetic acid, citric acid, glycolic acid, lactic acid, succinic acid, malic acid, or the like, or an inorganic acid such as hydrochloric acid, sulfuric acid, phosphoric acid, and nitric acid. In addition, it is possible to adjust the pH of the composition by using a metal hydroxide such as sodium carbonate, sodium hydroxide, an alkaline earth metal hydroxide, a carbonate or ethanolamine.

Since the chelating agent is capable of forming an insoluble complex with oxygen, nitrogen, or various metal ions, and inactivating various metal ions, the chelating agent may be included in the composition to enhance the steril-ization and disinfection effect, and disodium EDTA, triso-dium EDTA, sodium pyrophosphate, etidronate, glucuronic acid, gluconic acid, cyclodextrin, etc. may be used as the chelating agent.

The enzyme is capable of inhibiting metabolism of micro-organisms and decomposing metabolites of microorganisms, and include enzymes capable of decomposing various com-ponents such a protease, a lipase, an amylase, a hydrolase, a cellulase, etc. In addition, enzyme stabilizers such as benzamidine hydrochloride and boric acid may also be additionally included to prevent inactivation of enzymes due to physical effects, oxidation or decomposition.

Representative examples of the bleaching agent include peroxides such as sodium percarbonate, or phthalimido-peroxy-hexanoic acid, persulfate, or peroxoborate.

The builder is capable of increasing detergency for microorganisms and various contaminants that may be ingested by microorganisms, and representative examples thereof include sodium polyphosphate, sodium carbonate, sodium silicate, sodium borate, and nitrilotriacetic acid di-salt.

In addition, the composition for disinfection may further include flavoring agents, preservatives, dyes, corrosion inhibitors, and the like, and commonly used components may be used.

The composition for disinfection may be prepared by adding the above additives in various amounts depending on the intended use and conditions, and preferably the additives may be added in a ratio of 0.1 wt % to 5 wt %.

An anti-freezing agent may be additionally added to use the composition for disinfection stably even in cold weather that is below −10° C. By including the anti-freezing agent, various coronavirus infectious diseases that may occur even when temperature is very low in winter may be effectively prevented, even when preparing the composition as a liquid.

For the anti-freezing agent, propylene glycol, citric acid anhydrous, glycerin, etc. may be used, and propylene glycol, which is non-toxic and stable even when exposed to animals or humans, may be preferably used, and the anti-freezing agent may be added in an amount of about 5 wt % to about 25 wt %, with respect to the total weight of the composition. When a content of the anti-freezing agent is less than about 5 wt %, the anti-freezing effect is insignificant, and when a content exceeds about 25 wt %, a change in physical properties may occur.

Still another aspect is to provide a food composition for preventing or improving a coronavirus infection or infectious disease including the nano-sized graphene oxide or a complex thereof. The same parts as described above also apply to the composition.

The term "improvement", used herein, refers to any action improving or beneficially changing a coronavirus infectious disease by administration of the composition.

The term "food", used herein, refers to meat, sausage, bread, chocolate, candies, snacks, confectionery, pizza, ramen, other noodles, gums, dairy products including ice cream, various soups, beverages, tea, drinks, alcoholic beverages, vitamin complexes, dietary supplements, health functional foods, and health foods, and includes all foods in a general sense.

The food may be prepared by a method commonly used in the art, and may be prepared by adding raw materials and components commonly added in the art when being prepared. In addition, any formulation of food may be prepared without limitation as long as it is a formulation recognized as a food. The food composition may be prepared in various types of dosage forms, and unlike general drugs, has an advantage of not having side effects that may occur when taking a drug for a long period of time since food is used as a raw material, and has excellent portability, and therefore, the food of the present disclosure may be taken as a supplement to enhance an effect of improving intestinal environment.

The term "health functional food", used herein, refers to food manufactured and processed using raw materials or ingredients useful for the human body according to Health Functional Food Act No. 6727, and the term 'functionality' refers to obtaining useful effects for health purposes such as regulating nutrients or physiological effects with respect to the structure and function of the human body.

The health food means a food having an effect of active health maintenance or promotion compared to general food, and the term 'health supplement food' means a food for the purpose of health supplementation. In some cases, the terms health functional food, health food, and health supplement food may be used interchangeably. Specifically, the health functional food is a food prepared by adding the composition of the present disclosure to food materials such as beverages, teas, spices, gum, and confectionery, or by preparing the composition as a capsule, a powder, a suspension, etc. The health functional food brings a specific heath effect when ingested, but unlike general drugs, the food has an advantage of having no side effect that may occur when taking a drug for a long time because food is used as a raw material.

The food composition may further include a physiologically acceptable carrier, a type of the carrier is not particularly limited and any carrier commonly used in the art may be used.

In addition, the food composition may include additional ingredients that are commonly used in food compositions to improve odor, taste, appearance, and the like. For example, vitamins A, C, D, E, B1, B2, B6, and B12, niacin, biotin, folate, pantothenic acid, and the like may be included. In addition, minerals such as zinc (Zn), iron (Fe), calcium (Ca), chromium (Cr), magnesium (Mg), manganese (Mn), copper (Cu), and chromium (Cr) may be included. In addition, amino acids such as lysine, tryptophan, cysteine, and valine may be included.

In addition, the food composition may include food additives such as preservatives (potassium sorbate, sodium benzoate, salicylic acid, sodium dehydroacetate, etc.), disinfectants (bleaching powder and high bleaching powder, sodium hypochlorite, etc.), antioxidants (butylhydroxyanisole (BHA), butylhydroxytoluene (BHT), etc.), coloring agents (tar pigment, etc.), color formers (sodium nitrite, sodium acetate, etc.), bleaches (sodium sulfite), seasonings (mono sodium glutamate (MSG), etc.), sweeteners (dulcin, cyclamate, saccharin, sodium, etc.), flavorings (vanillin, lactones, etc.), swelling agents (alum, D-potassium hydrogen tartrate, etc.), strengthening agents, emulsifiers, thickeners, coating agents, gum base agents, defoaming agents, solvents, improving agents, etc. The additive may be selected according to a type of food and used in an appropriate amount.

The food composition may be added as it is or used together with other foods or food ingredients, and may be appropriately used according to a method in the art. The mixed amount of the active ingredient may be suitably determined according to its purpose (prevention, health or therapeutic treatment). In general, in preparing food or beverage, the food composition of the present disclosure may be added in an amount of 50 parts by weight or less, specifically 20 parts by weight or less with respect to the food or beverage. However, when consumed for a long period of time for health and hygiene purposes, it may contain an amount less than the above range, and since there is no problem in terms of safety, the active ingredient may be used in an amount exceeding the above range.

As an example of the food composition, the food composition may be used as a health drink composition, and in this case, the drink may contain various flavoring agents or natural carbohydrates as an additional component like a drink in the art. The above-mentioned natural carbohydrates include monosaccharides such as glucose and fructose; disaccharides such as maltose and sucrose; polysaccharides such as dextrin and cyclodextrin; or sugar alcohols such as xylitol, sorbitol, or erythritol. Natural sweeteners such as taumatin, stevia extract; and synthetic sweeteners such as saccharin or aspartame may be used as a sweetener. A ratio of the natural carbohydrate may be generally about 0.01 g to about 0.04 g, or specifically about 0.02 g to about 0.03 g per 100 mL of the health beverage composition of the present disclosure.

In addition to the above, the health beverage composition may include various nutrients, vitamins, electrolytes, flavoring agents, colorants, pectic acid, pectic acid salts, alginic acid, alginic acid salts, organic acids, protective colloidal thickeners, pH adjusters, stabilizers, preservatives, glycerin, alcohol, a carbonating agent, and the like. In addition, the health beverage composition may contain pulp for preparing natural fruit juice, fruit juice beverage, or vegetable beverage. These components may be used independently or in combination. Although a ratio of these additives is not very important, it is generally selected in a range of about 0.01 parts by weight to about 0.1 parts by weight per 100 parts by weight of the health beverage composition of the present disclosure.

The food composition may include the graphene oxide in various wt % to exhibit an effect of prevention or improvement for a coronavirus infection or infectious disease, specifically about 0.00001 wt % to about 100 wt % or about 0.01 wt % to about 80 wt %, with respect to the total weight of the food composition.

Still another aspect is to provide a feed composition for preventing or improving a coronavirus infection or infectious disease including the nano-sized graphene oxide or a complex thereof. The same parts as described above also apply to the composition.

The term "feed", used herein, may refer to any natural or artificial diet, meal, or a component of a meal for or suitable for an animal to eat, ingest, and digest.

A type of the feed is not particularly limited, and feed commonly used in the art may be used. Non-limiting examples of the feed include plant feeds such as grains, root/fruits, food processing by-products, algae, fibers, pharmaceutical by-products, oils and fats, starches, gourds or grain by-products; and animal feeds such as proteins, inorganic materials, oils and fats, minerals, single cell proteins, zooplanktons, or food. These may be used alone or in combination of two or more.

The feed composition may further include known additives that may be added to kill viruses depending on the formulation. The feed composition may be in a form of a highly concentrated solution, powder or granules. The feed composition may further include any protein-containing organic flour commonly used to meet dietary needs of animals. The feed composition may be used by adding the same to animal feed by dipping, spraying, or mixing.

The feed composition may further include substances exhibiting various effects, such as nutrient supplementation and weight loss prevention, enhancement of digestibility of fibers in the feed, improvement of oil quality, prevention of reproductive disorders and improvement of fertility, prevention of high temperature stress in summer. For example, mineral preparations such as sodium bicarbonate, bentonite, magnesium oxide, and complex minerals, trace minerals such as zinc, copper, cobalt, and selenium, vitamins such as kerotene, vitamin E, vitamins A, D, E, nicotinic acid, and vitamin B complex, protective amino acids such as methionine and lyic acid, protective fatty acids such as fatty acid calcium salt, live bacteria and yeasts such as probiotics (lactic acid bacteria), yeast cultures, and mold fermented products may be further included.

The feed composition may be applied to a number of animal diets including diets of mammals and poultry, that is, in feed and drinking water.

The feed composition may include all of the materials added to feed (that is, feed additives), feed raw materials, or the feed itself fed to an animal.

Another aspect is to provide a method for preventing or treating a coronavirus infection or infectious disease, including administering the pharmaceutical composition including the nano-sized graphene oxide or a complex thereof to a subject. The same parts as described above also apply to the method.

The term "subject", used herein, may include, without limitation, mammals including mice, livestock, humans, etc., farmed fish, etc., which have, or are at a risk of having a coronavirus infection or infectious disease, specifically, the subject may be a mammal, including mice, rats, dogs, pigs, cats, cows, horses, monkeys, sheep, chickens, guinea pigs, camels, bats, birds, pangolins, and humans.

An effective amount of the pharmaceutical composition may vary depending upon the patient's condition and body weight, severity of the disease, formulation of the drug, route and duration of administration, etc., and may be appropriately selected by those skilled in the art. The dosage of the pharmaceutical composition is within a range of about 0.001 mg/kg to about 100 mg/kg, about 0.01 mg/kg to about 10 mg/kg, or about 0.1 mg/kg to about 1 mg/kg, and may be administered once a day, multiple times a day, or once a several days.

The pharmaceutical composition may be administered alone or in combination with other pharmaceutically active compounds.

The pharmaceutical composition may be administered to a subject by various routes within a range that it may reach a target tissue. The administration may be oral, or parenteral administration. The administration may be by, for example, oral, rectal, intravenous, intraarterial, intraperitoneal, intramuscular, intrasternal, transdermal, topical, intraocular, or intradermal routes. However, when the pharmaceutical composition is administered orally without being formulated, the graphene oxide may be denatured or decomposed by gastric acid, and thus, an oral composition may be administered orally in a form in which the active ingredients are coated or formulated to be protected from degradation in the stomach, or in a form of an oral patch. In addition, the composition may be administered by any device capable of transporting the active substance to a target cell.

The pharmaceutical composition may be administered one time or multiple times in a pharmaceutically effective amount. In this regard, the composition may be formulated and administered in a form of a solution, powder, aerosol, injection, infusion solution (Ringer's solution), capsule, pill, tablet, suppository, or patch.

Another aspect provides a method for disinfecting coronavirus including spraying, applying, scattering, sprinkling, washing, or a combination thereof with a composition for anti-coronavirus disinfection including a nano-sized graphene oxide or a complex thereof in the air, on a surface of an object, or on a mammal other than a human. The same parts as described above also apply to the method.

The method may disinfect coronavirus by spraying, scattering, or sprinkling the composition for disinfection, or applying the composition for disinfection on a surface of an object, or washing an object or a body with the composition for disinfection.

Advantageous Effects of Disclosure

Since a nano-sized graphene oxide or a complex thereof has an anti-coronavirus activity, the graphene oxide may be used for prevention or treatment of a coronavirus infection and infectious disease, or disinfection of coronavirus.

BRIEF DESCRIPTION OF DRAWINGS

FIG. 1 is a diagram schematically showing a method of synthesizing nanoGO according to the present disclosure.

FIG. 5 is a diagram showing antiviral activity against PEDV and BCoV of nanoGO prepared by using various dilution factors. Marked letters indicate statistically significant differences between different dilution factors within each group (p<0.05), and asterisks indicate significant differences between the groups (*: p<0.05; **: p<0.01).

MODE OF DISCLOSURE

Hereinafter, the disclosure will be described in more detail through embodiments. However, these embodiments are intended to illustrate the present disclosure, and the scope of the present disclosure is not limited to these embodiments.

Example 1. Preparation of Nano Graphene Oxide (nanoGO)

Figure 1:
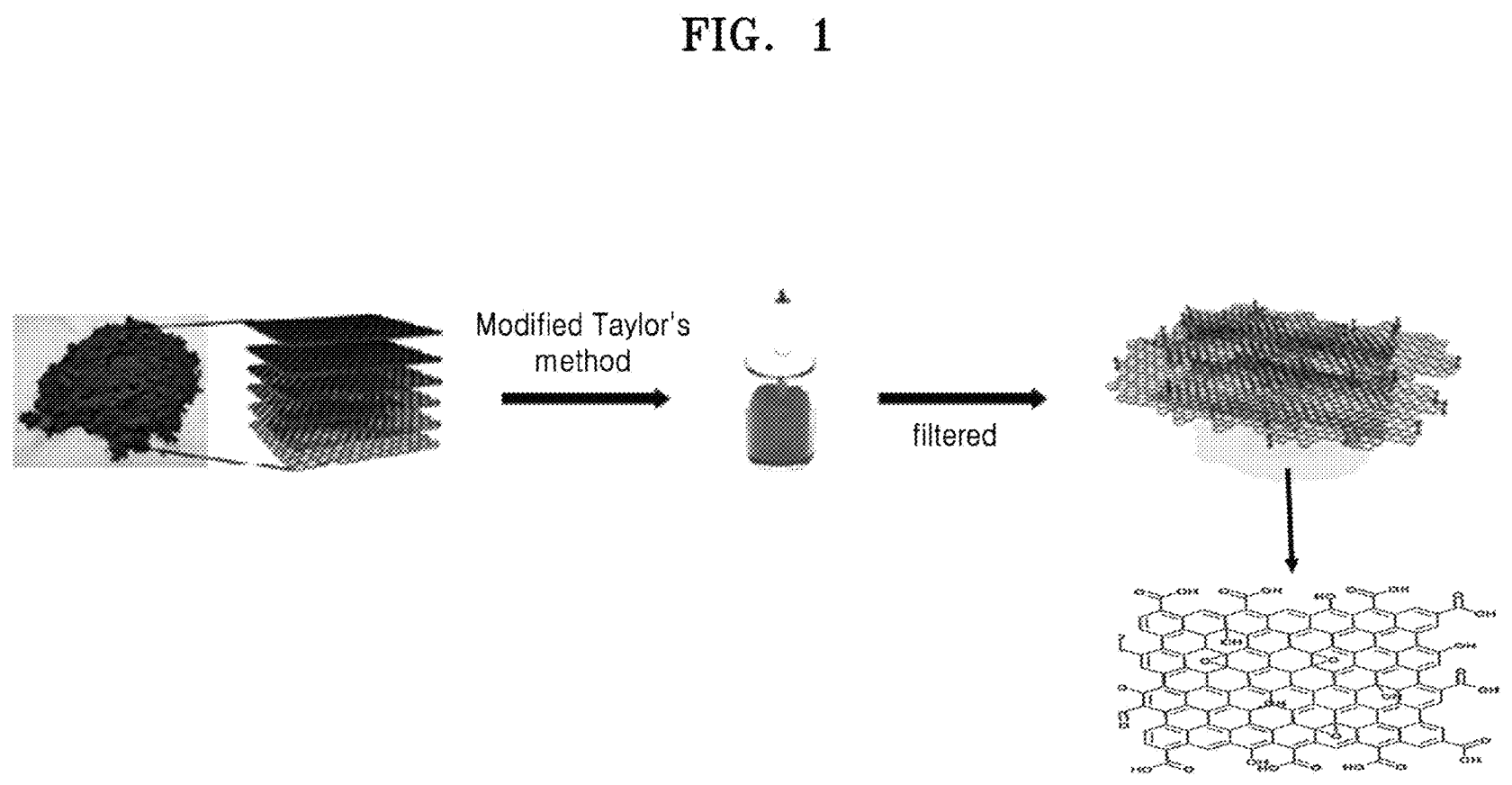

An uncontaminated graphene oxide (GO) was synthesized by using the modified Taylor's method (FIG. 1).

Specifically, high-purity graphite, sodium nitrate ($NaNO_3$) and sulfuric acid ($H_2SO_4$) were mixed, and potassium permanganate ($KMnO_4$) was mixed with the mixture on an ice water bath, and the mixture was rotated at a constant rotational speed (swelling effect of graphite occurs due to the rotation) for a certain period of time. After that, in order to apply a shearing force to the expanded graphite, a constant rotational force was applied for a certain time to facilitate separation between the layers. Then, hydrogen peroxide ($H_2O_2$) was added to the mixture and centrifuged to produce a graphite oxide. Distilled water solution (3 mg/ml) was added to the graphite oxide, and interlayer separation was performed by tip-sonicating for at least 1 hour to prepare a graphene oxide. The prepared graphene oxide was freeze-dried to prepare a dried graphene oxide.

The prepared graphene oxide was vacuum-filtered with a cellulose nitrate membrane filter (0.45 μm, GE Healthcare) to prepare a nano graphene oxide (nanoGO). In this example, a nanoGO solution (3 mg/mL) at a concentration of 1% was prepared as a standard, and a concentration (%) thereof was adjusted as necessary.

Example 2. Characterization of Nano Graphene Oxide (nanoGO)

In order to identify a size and shape of the nanoGO prepared in Example 1, scanning electron microscope (SEM) and transmission electron microscope (TEM) imaging analyses were performed.

Figure 2:
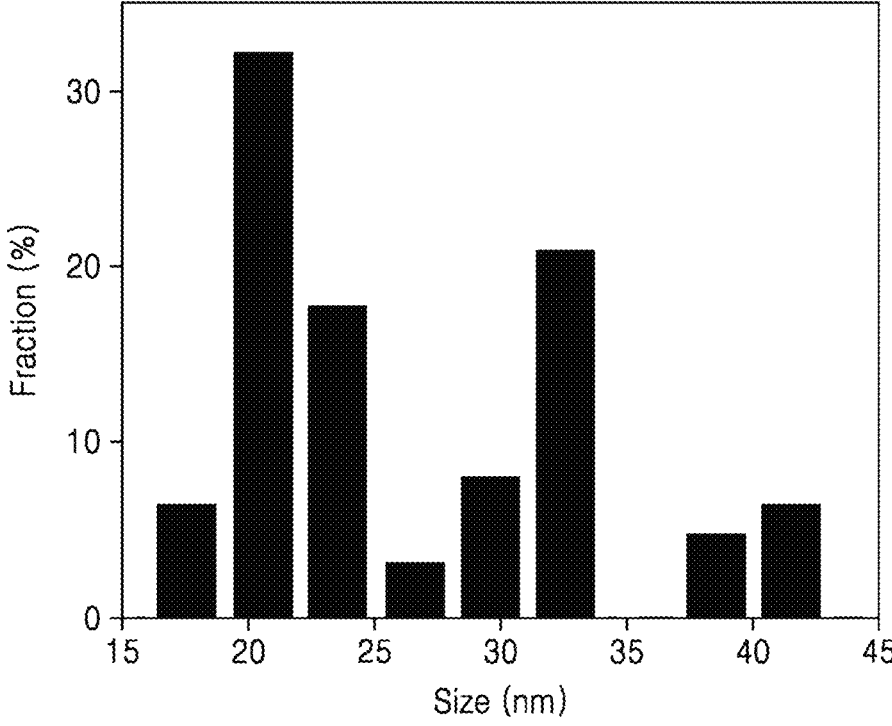
FIG. 2 is a diagram showing particle size distribution calculated from an SEM image of nanoGO.
Figure 3:
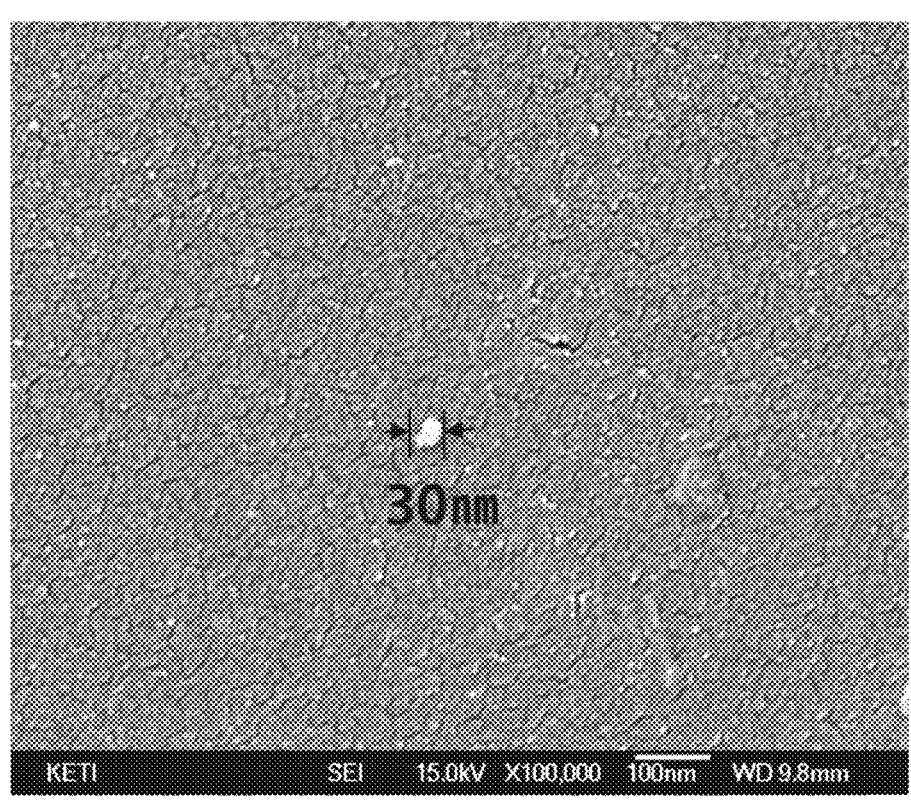
FIG. 3 is a diagram showing an SEM image of nanoGO.
Figure 4:
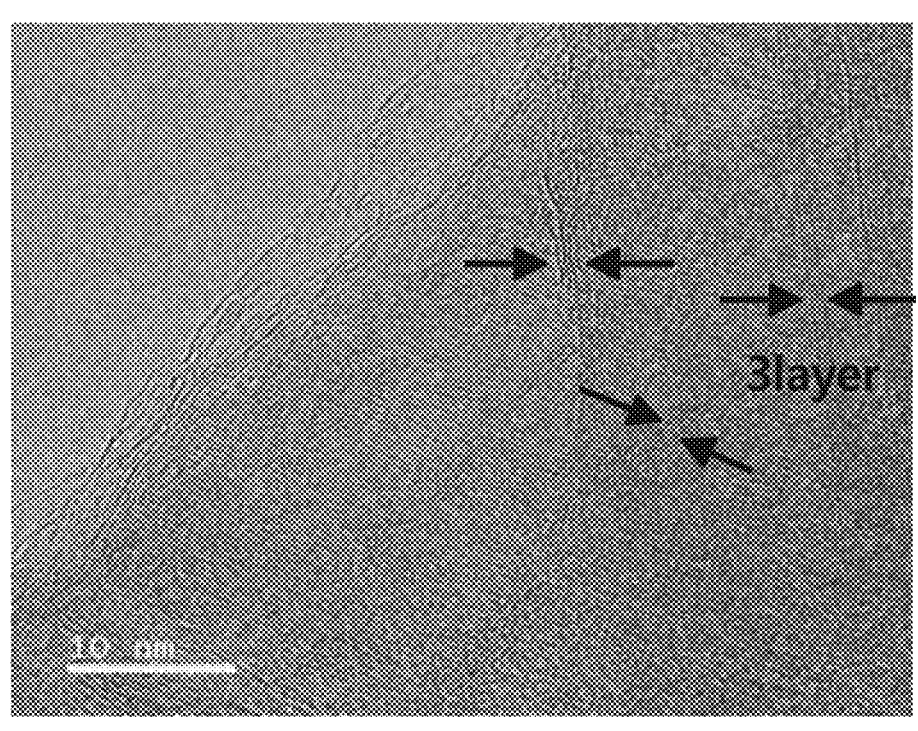
FIG. 4 is a diagram showing a TEM image of nanoGO.

As a result of the analyses, it was confirmed that the size of the nanoGO prepared in Example 1 exhibited a distribution of about 15 nm to about 45 nm (FIG. 2), and the shape was analyzed through the SEM imaging and TEM imaging (FIGS. 3 and 4).

Example 3. Identification of Cytotoxicity of Nano Graphene Oxide (nanoGO)

In order to identify cytotoxicity of the nanoGO prepared in Example 1, the following experiment was performed.

Specifically, nanoGO solutions prepared by using various dilution factors were added to Vero E6 cells (ATCC-1586), and cytotoxicity was measured by a CCK8 assay.

As a result, as shown in Table 1 below, it was confirmed that cytotoxicity did not appear at 1% nanoGO solution and all dilution factors thereof.

TABLE 1

| Dilution factor | 1x | 10x | 20x | 40x | 80x | 160x | 320x | 640x |
|---|---|---|---|---|---|---|---|---|
| Nano-oxide graphene | Δ | Δ | Δ | — | — | — | — | — |
| | Δ | Δ | Δ | — | — | — | — | — |

(Δ: Slightly cytotoxic. The experiments were conducted in duplicate)

Example 4. Confirmation of Antiviral Effect of Nano Graphene Oxide (nanoGO) Against PEDV and BCoV In order to confirm antiviral activity of the nano graphene oxide prepared in Example 1 against coronavirus, experiments were conducted on porcine epidemic diarrhea virus (PEDV) and bovine coronavirus (BCoV), which are well-known coronaviruses that cause a disease in animals.

First, the 1% nanoGO solution prepared in Example 1 was diluted by 50 to 800 times in Dulbecco's Modified Eagle Medium (DMEM) supplemented with 5% FBS. Each dilution was mixed with an equal volume of PEDV (DR13 strain) or BCoV (BC94 strain) having a titer of $10^7$ $TCID_{50}$/ML and incubated at room temperature for 60 minutes. PEDV and BCoV treated with nanoGO were titrated by using Vero cells. The maximum dilution factor at which the virus titer in the nanoGO-treated group decreased to 4.0 log 10 $TCID_{50}$/ml or more (death and inactivation) compared to virus infectivity in the control group was determined as an effective dilution factor (according to Korean Animal and Plant Quarantine Agency Notice No. 2018-16 (2018 May 31) Efficacy Test Guidelines). In addition, the antiviral effect of nanoGO was expressed as an inhibition rate (%) and was calculated as follows: [log 10 ($TCID_{50}$/ml of virus)–log 10 ($TCID_{50}$/ml of nanoGO-treated group)]/(log 10 ($TCID_{50}$/ml of virus)×100%.

As a result, as the dilution factor of nanoGO increased (1/50 to 1/800), a titer of PEDV/BCoV was observed to be increased from 0.0 to 6.3/6.4 log 10 $TCID_{50}$, and to gradually approach the titer of the control group (mock) not treated with nanoGO (6.6 log 10 $TCID_{50}$), and it was confirmed that 100-fold diluted nanoGO blocked virus replication more efficiently. Specifically, the virus titer of the nanoGO-treated groups (1.8 for PEDV, 2.5 for BCoV) was reduced by at least 4 log 10 compared to the control group (Table 2). Therefore, it may be seen that nanoGO exhibits antiviral activity against PEDV/BCoV in a dose-dependent manner.

TABLE 2

| Condition of treatment | NanoGo dilution factor | PEDV Average titer (log10 TCID$_{50}$) | BCoV Average titer (log10 TCID$_{50}$) |
|---|---|---|---|
| Virus + | 1/50 | 0.0 | 0.0 |
| nanoGO | 1/100 | 1.8 | 2.5 |
| | 1/150 | 2.8 | 3.9 |
| | 1/200 | 3.9 | 4.8 |
| | 1/250 | 4.4 | 5.2 |
| | 1/300 | 5.1 | 5.5 |
| | 1/400 | 5.6 | 5.8 |
| | 1/500 | 6.0 | 6.3 |
| | 1/600 | 6.2 | 6.3 |
| | 1/800 | 6.3 | 6.4 |
| Virus only | NA* | 6.6 | 6.6 |

[*NA: Not applicable: the underlined indicate the maximum dilution factor]

Figure 5:
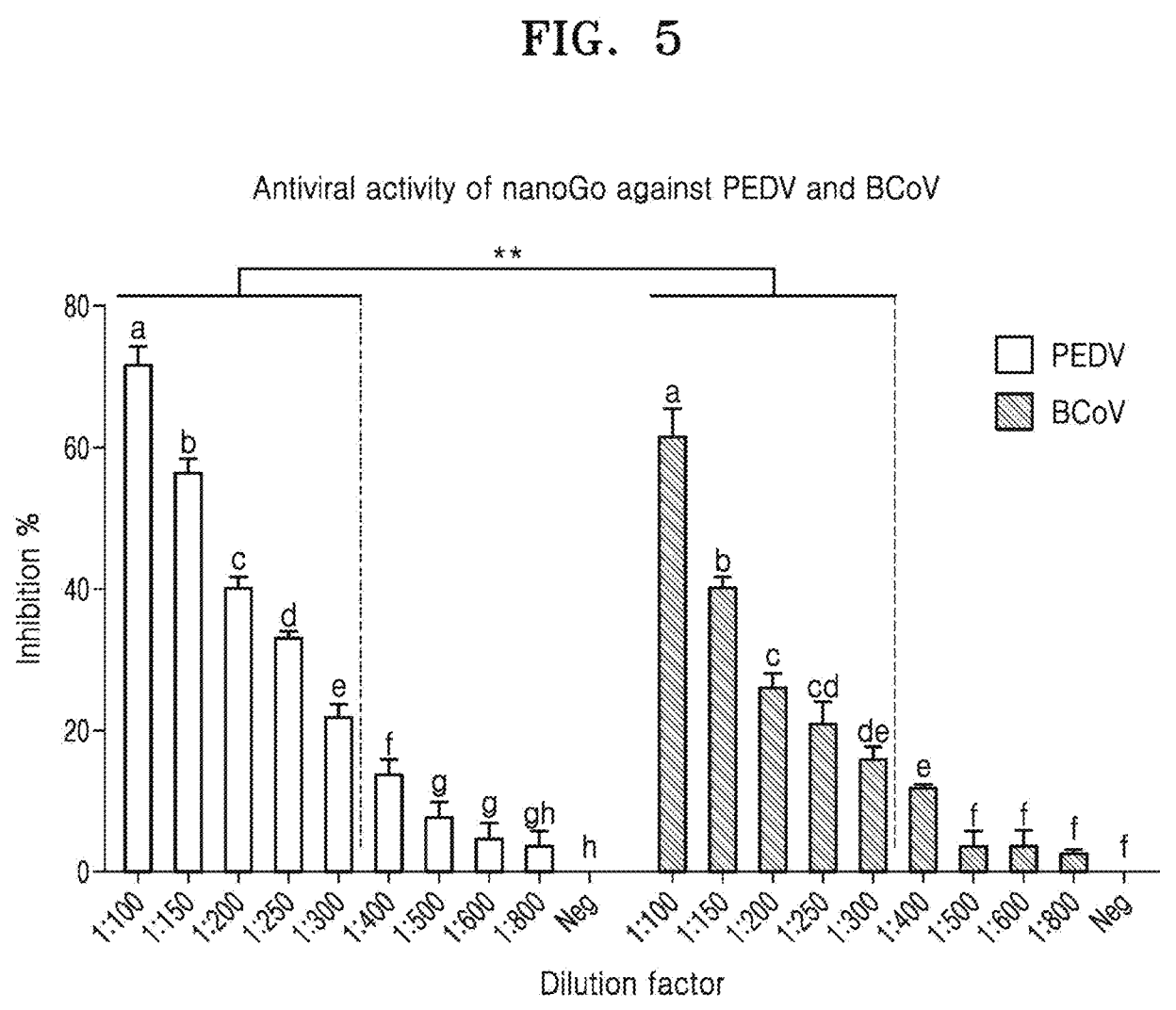

Next, as a result of calculating inhibition rates based on the results of the antiviral inhibitory effect, it was confirmed that the highest antiviral activity of nanoGO against PEDV and BCoV was 72.1% and 61.9%, respectively, when diluted at a rate of 1/100-fold, and when the concentration of the nanoGO solution was diluted to 1/800, antiviral activity against PEDV and BCoV was hardly observed (p>0.05). In addition, nanoGO showed a more effective antiviral activity against PEDV than BCoV up to 1/300-fold dilution (p<0.01) (FIG. 5).

Next, to analyze/detect replication of live viruses of PEDV and BCoV after a nanoGO treatment, immunofluorescence assays (IFA) were performed. Specifically, nanoGO diluted by a specific factor (1/50, 1/100, and 1/800) was treated to PEDV or BCoV, and the viruses were inoculated into Vero cells, respectively. An untreated control group without PEDV or BCoV was used as a negative control (mock), and a group inoculated with only PEDV or BCoV without nanoGO treatment was used as a positive control (virus). 24 hours after the virus inoculation, an immunofluorescence analysis was performed by using a PEDV IFA kit (Median Diagnostics) and BCoV primary antibodies (Median Diagnostics), and a statistical analysis was performed by using GraphPad Prism version 8.0.2.

Figure 6:
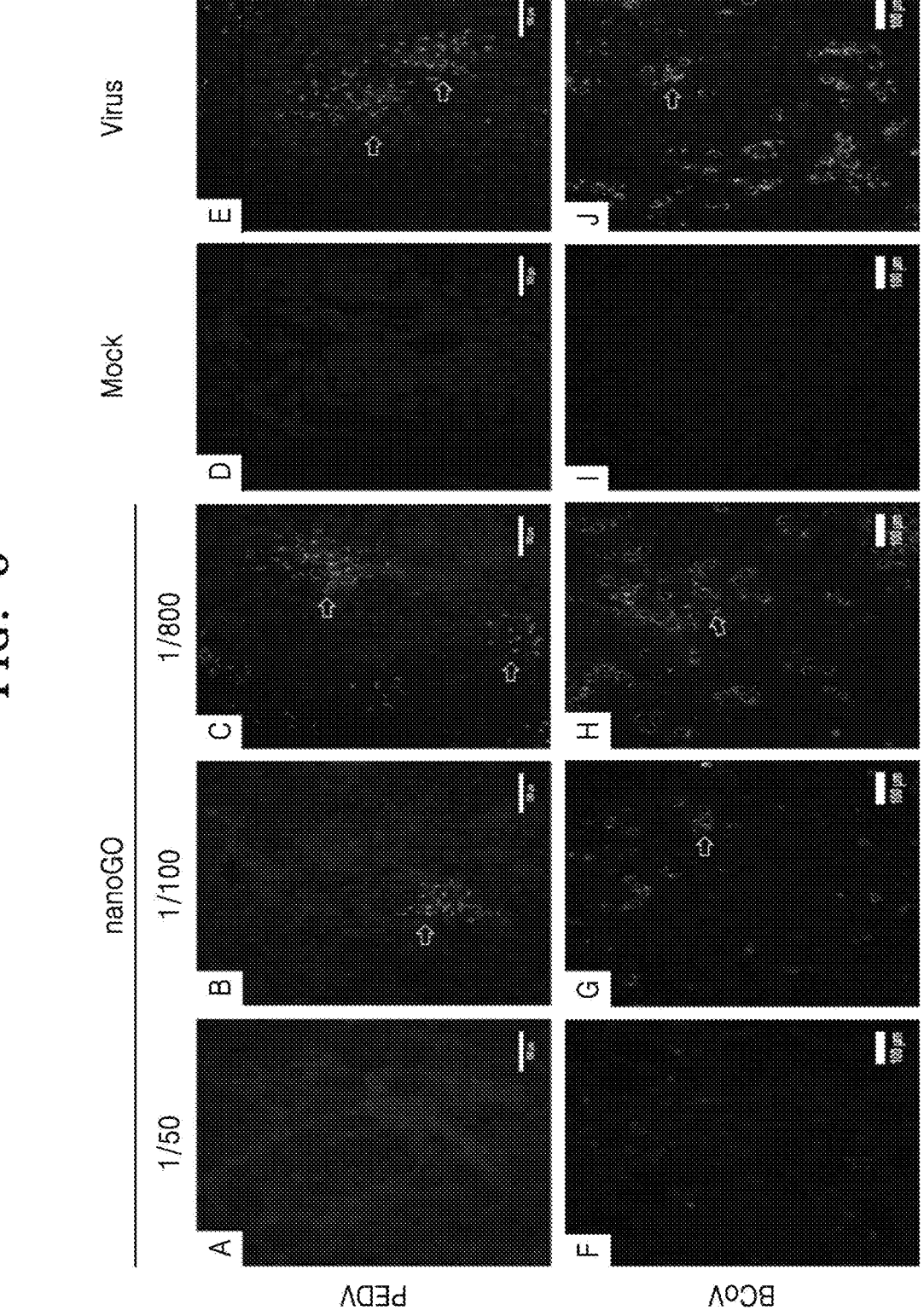
FIG. 6 is a diagram showing replication efficiency of PEDV and BCoV after nanoGO incubation through immunofluorescence assay (IFA). Cells with a fluorescent signal (marked with arrows) indicate that the cells are infected with a virus, and the greater the number of fluorescent cells, the greater the amount of viral replication.

As a result, PEDV and BCoV-infected cells (green fluorescence) were not observed at low dilutions (1/50) of nanoGO (A and F of FIG. 6), and viruses could not be completely inactivated from dilution factors of 100 or more, however, it was confirmed that the viruses were reduced compared to the positive control (B to C of FIG. 6, and G to H of FIG. 6).

Example 5. Confirmation of Antiviral Effect of Nano Graphene Oxide (nanoGO) Against SARS-CoV-2

In order to confirm an antiviral activity of the nano graphene oxide prepared in Example 1 against SARS-CoV-2, the corona virus that causes COVID-19, the following experiment was performed.

Specifically, a neutralization test was performed to evaluate the antiviral activity of nanoGO against SARS-CoV-2. First, the 1% nanoGO solution prepared in Example 1 was serially two-fold diluted with DMEM supplemented with 5% FBS (2-fold to 4096-fold dilution). Then, SARS-CoV-2 (BetaCoV/Korea/KCDC03/2020) of 25 TCID$_{50}$/ml was mixed with the diluted nanoGO in the same volume, and the mixture was incubated at 37° C. for 60 minutes. After that, Vero E6 cell monolayers were infected with 0.1 ml of a nanoGO mixture, respectively, and the presence or absence of cytopathic effect (CPE) was monitored daily for 5 days. A neutralizing titer was expressed as a reciprocal of the highest dilution factor that induces inhibition of CPE. All experiments related to SARS-CoV-2 were performed at the BL3 facility located at Chonbuk National University's Research Center for Infectious Diseases Common for Humans and Animals.

Figure 7:
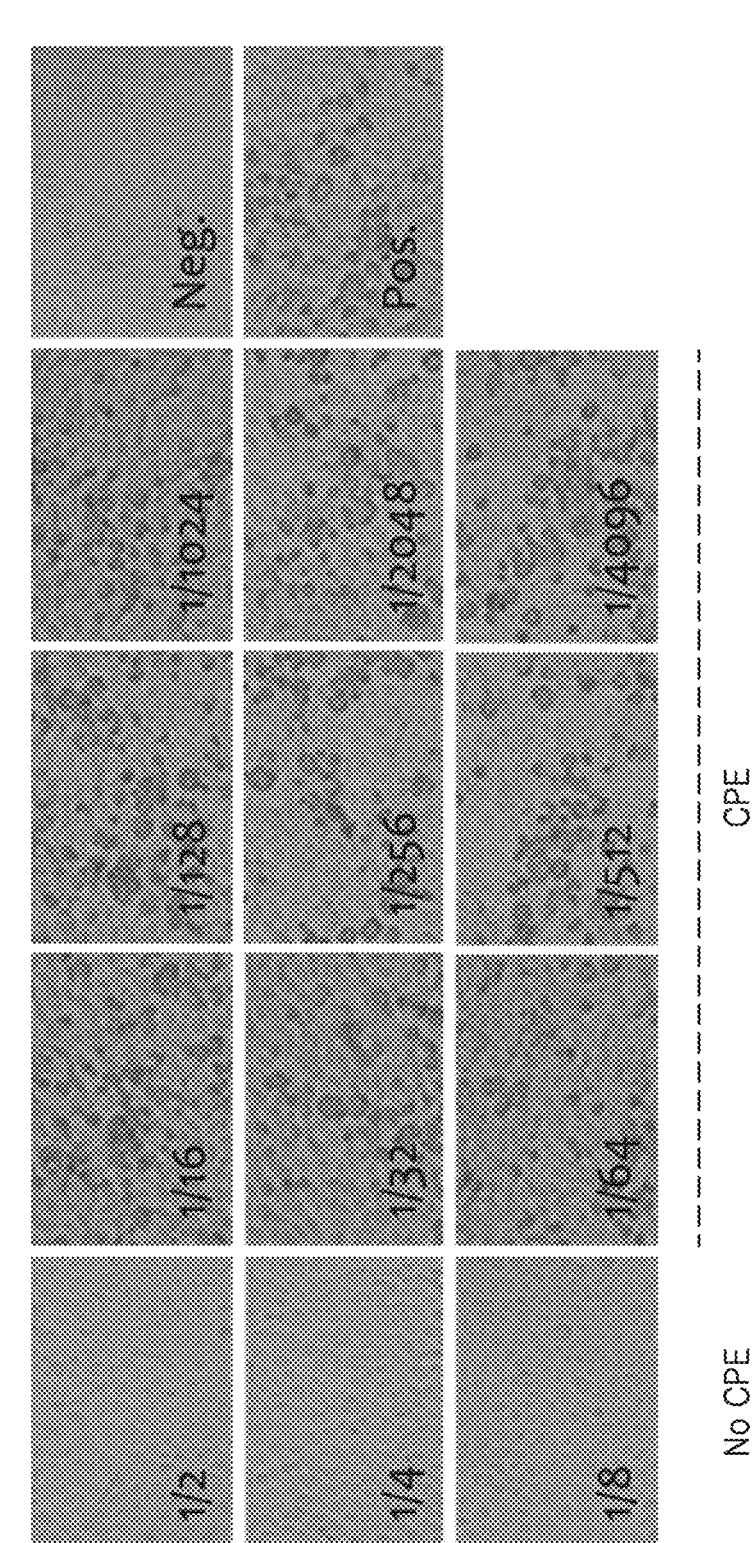
FIG. 7 is a diagram showing antiviral activity of nanoGO at various concentrations against SARS-CoV-2, based on test results of cytopathic effects (CPE).

As a result, it was confirmed that nanoGO completely inhibited SARS-CoV-2 replication at a dilution rate of 1/2 to 1/8 (CPE was not found) (FIG. 7). Therefore, it may be seen that a nano graphene oxide has an anti-COVID-19 coronavirus effect.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

The invention claimed is:

1. A method for preventing or treating a coronavirus infection or infectious disease, comprising administering a pharmaceutical composition comprising nano-sized graphene oxide or a complex thereof to a subject in need thereof, wherein the nano-sized graphene oxide has a diameter of 100 nm or less.

2. The method for preventing or treating a coronavirus infection or infectious disease of claim 1, wherein the graphene oxide has a thickness of about 0.3 nm to about 10 nm.

3. The method for preventing or treating a coronavirus infection or infectious disease of claim 1, wherein the graphene oxide is present as a homogenized dispersion.

4. The method for preventing or treating a coronavirus infection or infectious disease of claim 1, wherein the coronavirus is selected from the group consisting of alphacoronaviruses, betacoronaviruses, gammacoronaviruses, and deltacoronaviruses.

5. The method for preventing or treating a coronavirus infection or infectious disease of claim 1, wherein the coronavirus is porcine epidemic diarrhea virus (PEDV), canine coronavirus (CCV), feline infectious peritonitis virus (FIPV), bovine coronavirus (BCoV or BCV), avian infectious bronchitis virus (IBV), transmissible gastroenteritis coronavirus (TGEV), severe acute respiratory syndrome coronavirus (SARS-COV), severe acute respiratory syndrome coronavirus 2 (SARS-COV-2), middle east respiratory syndrome coronavirus (MERS-CoV), or a combination thereof.

6. The method for preventing or treating a coronavirus infection or infectious disease of claim 1, wherein the coronavirus infectious disease is coronavirus cold, coronavirus enteritis, coronavirus diarrhea, coronavirus pneumonia, severe acute respiratory syndrome (SARS), middle east respiratory syndrome (MERS), coronavirus disease 2019 (COVID-19), acute respiratory distress syndrome (ARDS), avian infectious bronchitis, or a combination thereof.

7. A method for disinfecting coronavirus, comprising spraying, applying, scattering, sprinkling, washing, or a combination thereof with a composition for anti-coronavirus disinfection comprising nano-sized graphene oxide or a complex thereof in the air, on a surface of an object, or on a mammal, wherein the graphene oxide has a diameter of 100 nm or less.

8. The method for disinfecting coronavirus of claim 7, wherein the graphene oxide has a thickness of about 0.3 nm to about 10 nm.

9. The method for disinfecting coronavirus of claim 7, wherein the graphene oxide is present as a homogenized dispersion.

10. The method for disinfecting coronavirus of claim 7, wherein the coronavirus is selected from the group consisting of alphacoronaviruses, betacoronaviruses, gammacoronaviruses, and deltacoronaviruses.

11. The method for disinfecting coronavirus of claim 7, wherein the coronavirus is porcine epidemic diarrhea virus (PEDV), canine coronavirus (CCV), feline infectious peritonitis virus (FIPV), bovine coronavirus (BCOV or BCV), avian infectious bronchitis virus (IBV), transmissible gastroenteritis coronavirus (TGEV), severe acute respiratory syndrome coronavirus (SARS-COV), severe acute respiratory syndrome coronavirus 2 (SARS-CoV-2), middle east respiratory syndrome coronavirus (MERS-COV), or a combination thereof.

\* \* \* \* \*